United States Patent [19]

Bradbury et al.

[11] Patent Number: 4,865,842

[45] Date of Patent: Sep. 12, 1989

[54] PESTICIDAL COMPOSITION FOR WATER TREATMENT

[75] Inventors: Roderick S. Bradbury, Reading; Raymond J. Quinlan, Reading; Brian H. Most, Newbury, all of Great Britain

[73] Assignee: Novo Industri A/B, Bagsvaerd, Denmark

[21] Appl. No.: 161

[22] Filed: Jan. 2, 1987

[30] Foreign Application Priority Data

Jan. 6, 1986 [GB] United Kingdom ................. 8600190

[51] Int. Cl.$^4$ ...................... A01N 63/00; A01N 25/26; A01N 25/00

[52] U.S. Cl. ...................................... 424/93; 514/405; 514/408; 514/466; 514/468; 514/627

[58] Field of Search ................. 424/93, 405, 408, 466, 424/468, 43, 44; 514/627

[56] References Cited

U.S. PATENT DOCUMENTS 3,105,790 10/1963 Bartholomew et al. ............ 424/466
3,131,123 4/1964 Masquelir ............................ 424/466
4,000,258 12/1976 Shieh et al. ........................... 424/93
4,166,112 8/1979 Goldberg .............................. 424/93
4,431,834 2/1984 Cartwright ........................... 560/56
4,515,808 5/1985 Elliott ................................. 514/521

FOREIGN PATENT DOCUMENTS 2290844 7/1976 France ................................. 424/44
0122098 6/1985 Japan .
369891 11/1973 U.S.S.R. .
1172900 12/1969 United Kingdom .
2139893 11/1984 United Kingdom ................. 424/44

*Primary Examiner*—John W. Rollins
*Attorney, Agent, or Firm*—Rosen, Dainow & Jacobs

[57] ABSTRACT

A pesticidal formulation for treatment of water to control water borne pests such as mosquitoes and blackfly or water hyacynth comprises tablets, granules or the like containing in their interior one or more pesticidal ingredients together with one or more effervescence-initiation components and a surface active dispersant so formulated that, when added to the water to be treated, they are capable of dispersing the pesticidal ingredients at or near the surface of the water.

11 Claims, No Drawings

PESTICIDAL COMPOSITION FOR WATER TREATMENT

This invention relates to pesticidal formulations for control of water-borne insect pests, in particular mosquitoes and blackfly and other water-borne pests e.g. invasive plants, in particular water hyacinth.

The control of water borne pests such as mosquitoes and blackfly, where the larval and pupal forms live in water, is difficult for a number of reasons. Firstly, the use of generally toxic pesticides is contra-indicated in water containing other valued species. For this reason, a biological pesticide derived from *Bacillus thuringiensis*, especially *B.thuringiensis* var. israelensis, is of great interest. The bacteria contain a proteinaceous crystal toxin which is specifically toxic to mosquito species (Culicidae) and blackfly species (Simulidae). In particular, the endotoxin produced by *B. thuringiensis* var. israelensis serotype H-14 is used for this purpose and is specific to those species of insect which have (a) an alkaline gut (pH to 9) and (b) an enzyme complement suitable for degradation of the endotoxin crystal. In practice this means mosquitoes and blackfly only. Indeed, the *B. thuringiensis* pesticide is not harmful to organisms of the following types: Amphibia; Crustacea; Molluscs; Ephemeroptera; Hemiptera; Odonata, fish, annelid worms, flatworms, Diptera, Coleoptera, Hymenoptera, and Trichoptera. Furthermore, the toxin is completely non-toxic to humans and mammals and thus is entirely safe for use in drinking water supplies.

A second problem is that the larvae of mosquitoes and blackfly feed at or near the surface of the water. This means that the pesticide must be supplied in that region. It is of no use if the pesticidal composition sinks to the bottom of the water or is diluted and dispersed throughout the water system.

In order to solve these problems, solid formulations of *B. thuringiensis* toxins have comprised either wettable powders and the like for spraying onto water surfaces, or coated buoyant granules, in which the active material is adhering to the exterior of small particles which are of an appropriate density to remain at or near the water surface. Typically, the granules used are based on maize seeds (corn), porous clay or perlite granules and granules based on sand.

However, these granules have their own shortcomings. Floating granules are prone to wind drift, causing them to be driven towards the edges of open water, rather than remaining dispersed evenly across the water surface. Also, their relative lightness results in a tendency for them to lodge on foliage and thus not reach the water surface at all. On the other hand, coated sand granules tend to be too dense and do not spend long enough at the water surface.

An alternative solid formulation consists of "briquettes" which are claimed to have an activity for up to 30 days. In practice, these are found to give irregular or patchy control.

Apart from solid formulations, as described above, liquid formulations of *B. thiringiensis* have been proposed. For example, SU 369891-S describes a stabilised suspension of *B. thuringiensis* comprising an aqueous culture containing added oxyethylated di- and tri- esters of pentaerythritol with 6-12 carbon atom carboxylic acids. The non-ionic surfactant helps to prevent the bacilli from sinking. U.S. Pat. No. 4,166,112 describes a buoyant colloidal suspension of *B. thuringiensis* formed from a suspension of spores in dioxan containing an oil such as jojoba oil. However, the aqueous liquid formulations are heavy and require a whole cell culture rather than just the spores or the toxin crystals themselves, and solvents such as dioxan are undesirably toxic to aquatic species.

Apart from water-borne insect pests, other water-borne pests need to be controlled by application of a suitable pesticide to the water surface. Another major class of water-borne pest, especially in tropical areas, is aquatic plants. Particularly troublesome are the floating plants such as water hyacinth which clog waterways. Conventional spraying of herbicides over water is difficult, especially in windy conditions when drift is a problem. A solid formulation of a herbicide such as propanil which released the active material at the water surface would be very desirable.

The formulation must thus be able to dispense the pestidical ingredient(s) at or near the water surface and so must, in the water, exhibit a suitable degree of buoyancy and dispersibility. At the same time, it must not be prone to wind drift. We have now found that these requirements can be met by formulating the pesticidal ingredient(s) in a disintegrating effervescent presentation: the effervescence provides buoyancy, keeping the materials at or near the surface of the water, and also aids dispersion of the contents.

According to the present invention, therefore, there is provided a pesticidal formulation for water treatment comprising tablets, granules or the like containing in their interior one or more pesticidal ingredients together with one or more effervescence-initiating components and a surface active dispersant, and so formulated that, when added to the water to be treated, they are capable of dispersing the pesticidal ingredients at or near the surface of the water.

Dispersion occurs on the breakup of the tablet or granule and is ensured by the inclusion of a survace active dispersant, e.g. an anionic surfactant such as an alkylbenzene sulphonate, an alcohol sulfate, an ether sulfate, a phosphate ester, a sulphosuccinate, an alkane sulphonate, an olefin sulphonate or petroleum sulphonate, a sarcosinate or a taurate. The dispersant of choice is sodium dioctylsulphosuccinate.

The effervescence-initiating components can comprise any conventional effervescent couple, for example a solid acid and a carbonate or bicarbonate, for example citric or malic acid together with sodium bicarbonate. The pesticide, the effervescence-initiating components and the surface active dispersant are formulated into suitable solid bodies, for example tablets of 0.1 to 5 g weight e.g. 0.2 to 1 g; and granules of about 5 to 20 mg weight, e.g. 7.5 to 15 mg.

Buoyancy is considerably helped by the inclusion of low density buoyancy aids, for example, colloidal silica. Dispersion is improved by inclusion of a tablet disintegrant such as polyvinylpyrrolidone. In addition, tablets contain lubricants, binders and, if desired colouring agents, as required.

Granules can be formed by granulation of the pesticidal, effervesence-initiating and dispersant ingredients mentioned above in a paste formed from conventional granulating material, e.g. a filler such as china clay and a non-aqueous fluid, for example a high molecular weight polyethylene glycol, such as PEG 4,000. Water free conditions are of course essential, in order to avoid activation of the effervesence-initiators.

In a modification of the formulation according to this invention, small tablets or granules can be loaded into an intermittent release cartridge or the like so that over a period of days or weeks the water progressively comes in contact with batches of the tablets or granules. For example, a water-resistant cartridge with an open end can be charged with a number of tablets or granules. These can then be covered by a water soluble seal and another batch of tablets or granules loaded in followed by another water-soluble seal etc so that the cartridge comprises a sequence of compartments each containing tablets or granules and separated from each other by a water soluble seal. The cartridge should be so constructed that it sinks to the bottom of the water supply. After a short time, the water will dissolve away the first seal and the first batch of tablets or granules will be released and will rapidly rise to the surface as they effervesce and disintegrate. In due course the second seal will be dissolved and a fresh batch of tablets or granules will be released and so on. In this way, reinfestation of the water supply can be prevented without the need for additional visits to treat the water.

The pesticide of choice in the formulations according to the present invention will include a biological pesticide, i.e. a pesticide derived from a natural parasite or infective agent, in particular a bacterial toxin product which is selectively toxic to the insect species to be eradicated. Of particular importance is the toxin derived from *Bacillus thuringiensis* var. israelensis, in particular strain H-14. As this pesticide is highly selective, the compositions according to the present invention can be used to treat river and pond water where the fish or other animal life must be protected. Furthermore, since the material is non-toxic to humans and mammals, it can be safely used to treat drinking water supplies.

However, it is possible that in other applications, for example irrigation ditches, unwanted stagnant water etc, where toxicity is not such a problem, other organic chemical insecticides of botanical or synthetic origin, or herbicides, can be incorporated, for example natural or synthetic pyrethrins, phosphorus-based pesticides e.g. temephos, and herbicides such as propanil. For choice, however, the formulations according to the present invention will contain *B. thuringiensis*-based products in view of their well- recognised activity and safety.

Field trials of granules containing a *B. thuringiensis* var israelensis H-14 preparation were carried out as follows.

The experimental site was a drainage ditch which ran from the south to the sea in the north. The water within the ditch was stagnant except after heavy rain when it began to flow into the sea.

METHODS

The ditch was divided into five sections with wooden planks. Each section was made water-tight by packing mud around each of the planks. The surface area of the water in each of the sections was obtained by measuring the width of the ditch at water level at intervals of 1m, calculating the mean width and multiplying by the length of the section. Water samples were taken for subsequent analysis of pH, turbidity, and salinity. The air temperature and water temperature 5 cm beneath the surface were measured with a thermometer. The extent of surface vegetation, 'scum' etc. was estimated. A sample of larvae were taken and preserved in alcohol for identification. Ten dips were taken with a ladle (350 ml capacity with a 13 cm diameter rim) at approximately 0.5 m intervals in each section of the ditch. The number of each instar and whether they were alive or dead were recorded.

The northern-most section of ditch (nearest the sea) was labelled Section A, and so on to Section E, the most southerly (inland) section. Each section was treated as below:

Section A: treated with 30% less than recommended dose granules

Section B: treated with standard recommended dose granules (see below)

Section C: treated with 30% more than recommended dose granules

Section D: untreated Control

Section E: untreated, to be used as a larvae stock for bioassays.

The relevant quantities of granules were determined for each section according to the water surface area and the required treatment. The granules were applied evenly over the water surface in each of the three treated sections. After time intervals of 30 minutes, 1 hour, 2 hours, 24 hours, 48 hours and 96 hours after treatment, five 80 ml samples of water were taken at 0.5m intervals from sections A, B, C and D using a small ladle (40 ml capacity with a 6 cm diameter rim). Each sample was placed in a plastic bioassay (250 ml capacity, 8.5 cm diameter and 6 cm deep). The samples were sheltered from wind, rain and direct sunlight at outdoor temperature. Into each sample were placed 10 larvae (1st, 2nd and 3rd instars) obtained from the untreated section E. These samples were inspected at 24 hours, 48 hours and 96 hours and the number of dead larvae per sample counted.

As well as conducting bioassays, at 24 hours, 48 hours and 96 hours ten dips were taken from each of the sections, A, B, C and D as described above. The number of each instar and whether they were dead or alive was noted.

RESULTS

The surface of each of the sections of the ditch were covered with a thick mass of green algae. It was estimated that this algae covered 40% of the surface area of section A, 50% of section B, 50% of section C and 60% of section D. The bed of the ditch was composed of black smelly mud, an indication of high organic content. Crustacea such as *Cyclops* were abundant in each section indicated at high bacterial presence. The pH of the water was found to be 8.2. Turbidity was measured using a spectrometer at a wavelength of 315 nm and the sample was found to have an average absorbance value of 0.269, and an average light transmission value of 52.5% relative to distilled water. Salinity measured by the hydrometric method was found to be 5.9 parts/1000. The temperature varied greatly throughout the trial.

As the water surface of each of the sections was densely covered with gren algae, and fourth instar larvae were present, it was decided to use the higher recommended dose of 2 g granules per 10 $m^2$. The granules contained 600 ITU/mg (ITU reference standard 1PS—78 (WHO)—see Bulletin of the ESA, Spring 1984 pp 26–29). The surface areas of the sections and the quantities of the granules used were calculated as:

| | Surface Area | Recommended dose | Dose Applied |
|---|---|---|---|
| Section A | 2.21 $m^2$ | 0.442 g | 0.31 g (30% less than recommended) |
| Section B | 1.86 $m^2$ | 0.372 g | 0.37 g (recommended dose) |
| Section C | 1.72 $m^2$ | 0.344 g | 0.45 g (30% more than recommended dose) |
| Section D | 2.24 $m^2$ | 0.448 g | 0.00 g (control) |

RESULTS FROM DIPPING ASSAYS

It is clear from the following table that the proportion of dead larvae per dip increased after treatment in the treated sites, the control site remaining relatively free of dead larvae. The overall number of larvae per dip also decreased, which at first sight could be interpreted as being the result of the treatment. However, the means number of larvae per dip in the control pond also decreased. This was largely due to the drying up of the control pond and the larvae being caught in the mud or sheltering under the algae to prevent overheating and desiccation. The water level in sections A and B did not change to any noticable extent, however the level and surface areas of section C and D did change significantly. The drying up of these sections made sampling difficult and will have affected the number and distribution of larvae, so some inaccuracy will be found in the calculations of the effectiveness of the treatments.

Live larvae present in the treated section relative to the control pond (%)*

| | | Section A | Section B | Section C |
|---|---|---|---|---|
| Prior to | Actual | 44.8 | 59.8 | 60.3 |
| Treatment | Corrected | 100.0 | 100.0 | 100.0 |
| 24 h after | Actual | 22.9 | 15.5 | 28.7 |
| Treatment | Corrected | 51.1 | 38.5 | 47.6 |
| 48 h after | Actual | 18.8 | 14.6 | 10.4 |
| Treatment | Corrected | 41.2 | 24.4 | 17.3 |
| 96 h after | Actual | 28.6 | 19.0 | 14.3 |
| Treatment | Corrected | 63.7 | 31.9 | 23.7 |

The following formula (an extended Abbot's formula) was used to calculate the effectiveness of the treatments in terms of life larvae present in the treated ponds relative to the control pond at the time of sampling after treatment as a percentage:

$$\frac{N_t}{N_c} \times \frac{N_{co}}{N_{to}} \times 100$$

Where $N_t$ is the number of live larvae per dip in the treated site after treatment $N_c$ is the number of larvae per dip in the control site after treatmen of other sites has begun $N_{to}$ is the number of larvae per dip in the treated site before treatment $N_{co}$ is the number of larvae per dip in the control site before treatment of the other sites has begun By 48 hours the treatment had reduced the number of larvae to 42.1% in section A, 24.4% in section B, and 17.3% in section C (corrected values) relative to control site.

RESULTS FROM BIOASSAYS

Abbot's formula was used to determine the corrected mortality in each set bioassays:

$$\% \text{ mortality} = 100 - \left( \frac{\% \text{ survival in treated sample} \times 100}{\% \text{ survival in control sample}} \right)$$

The mortality in each of the replicate bowls within each treatment differed considerably in the samples taken on the day of application, possibly due to uneven dispersion of the product as a consequence of the dense algae covering much of the water surface.

It was evident that the water samples from the treated sites were effective agains the larvae with high mortalities after only 24 hours immersion. Practically complete mortality occurred after 96 hours immersion.

CONCLUSIONS

Both sets of data, from the dipping and bioassays clearly showed that the new formulation in highly effective against the British mosquito *Aedes detritus* even in sites with fairly high organic pollution and dense surface vegetation. The data from the dipping assays appeared to show a correlation between dosage and mosquito mortality. This was not apparent in the bioassay data. The bioassays sow that the potency of the formulation is greatly reduced 24 hours after application, and is non-existant after 48%. This is probably due to the small particle size of the *Bti* resulting in it sinking very rapidly, and also biodegradation.

The following Examples will illustrate the invention:

EXAMPLE 1

Effervescent Tablets (50% active ingredient)

Active ingredient: *Bacillus thuringiensis* var israelensis serotype H14.

Ingredients

| | | % w/w |
|---|---|---|
| Active ingredient | 2,000 ITU/mg primary powder | *50.0% |
| Surface active dispersant | sodium dioctylsulphosuccinate | 15.0% |
| Tablet disintegrant | polyvinylpyrrolidone | 4.0 |
| Buoyancy aid | silica | 5.0% |
| Lubricant | magnesium stearate | 1.0% |
| Binder | microcrystalline cellulose | 9.0% |
| Effervescence Initiators | citric acid (anhydrous) | 4.0% |
| | sodium bicarbonate | to 100% |

*To give a potency of 1,000 ITU/mg of tablet.

The tablet ingredients are mixed and compressed sufficiently to avoid crumbling during handling or in transit, but not so much as to cause the tablets to sink when applied to water. It has been found from measurements in the laboratory that a 5 g tablet with the following dimensions meets the required standards:

| | |
|---|---|
| Weight: | 5 g +/− 0.25 g |
| Length: | 40 mm |
| Width: | 13.5 mm |
| Thickness: | 12 +/− 0.60 mm |

Moisture content

The lowest possible moisture content is desirable to avoid deterioration of the tablets on storage. Moisture content is normally 2.5-3.5% as measured by the Dean & Stark method.

Effervescence

The tablets should float within 5 seconds of being applied to water at 20° C. and should start to effervesce immediately on the water surface.

EXAMPLE 2

100 mg Mini-tablets (15% active ingredient)

Ingredients

| | | % w/w |
|---|---|---|
| Active ingredient | 4,000 ITU/mg primary powder | *15.0% |
| Surface active dispersant | sodium dioctylsulphosuccinate | 15.0% |
| Tablet disintegrant | polyvinylpyrrolidone | 4.0% |
| Buoyancy aid | silica | 5.0% |
| Lubricant | magnesium stearate | 1.0% |
| Binder | microcrystalline cellulose | 9.0% |
| Effervescence Initiators | citric acid (anhydrous) | 12.0% |
| | sodium bicarbonate | to 100% |

*To give a potency of 600 ITU/mg of tablet.

The tablets are compressed as in Example 1.

EXAMPLE 3

Water dispersible granules (5% & 15% active ingredient)

Ingredients

| | | 5.0% | 15.0% |
|---|---|---|---|
| Active ingredient | 4,000 ITU/mg primary powder | 5.0%** | 15.0%* |
| Surface active dispersant | sodium dioctylsulphosuccinate | 15.0% | 15.0% |
| Binder | microcrystalline cellulose | 5.0% | 5.0% |
| Filler | china clay | 2.0% | 2.0% |
| Granulating liquid | PEG 4000 (molten) | approx 13.0% | 13.0% |
| Effervescence Initiators | Citric acid (anhydrous) | 15.0% | 12.5% |
| | Sodium bicarbonate | to 100% | to 100% |

**To give a potency of 200 ITU/mg
*To give a potency of 600 ITU/mg

Moisture content

The lowest possible moisture content is desirable to avoid deterioration of the granules on storage. Moisture content is normally 2.5-3.5% as measured by the Dean & Stark method.

Effervescence

The granules should float within 5 seconds of being applied to water at 20° C. and should start to effervesce immediately on the water surface.

Granule size

The granules are nominally 2 mm in diameter and up to approximately 5 mm in length, not more than 1% "fines" should pass a 1 mm sieve.

Density

Bulk density is normally 0.55+/−0.05 g/cc Packing density is normally 060+/−0.05 g/cc.

EXAMPLE 4

| 5% Temephos Tablets | |
|---|---|
| temephos technical | 5.0 |
| sodium dioctylsulphosuccinate | 15.0% |
| polyvinylpyrrolidnne | 5.0% |
| silica | 8.0% |
| magnesium stearate | 1.0% |
| microcrystalline cellulose | 10.0% |
| citric acid (anhydrous) | 14.0% |
| sodium bicarbonate | to 100% |

EXAMPLE 5

| 0.5% Pyrethrins Tablets | |
|---|---|
| 2.5% pyrethrins dust concentrate | 2.0% |
| sodium dioctylsulphosuccinate | 15.0% |
| polyvinylpyrrolidone | 4.0% |
| silica | 5.0% |
| magnesium stearate | 1.0% |
| microcrystalline cellulose | 9.0% |
| citric acid (anhydrous) | 16.0% |
| sodium bicarbonate | to 100% |

EXAMPLE 6

| 5% Temephos Granules | |
|---|---|
| temephos technical | 5.0 |
| sodium dioctylsulphosuccinate | 15.0% |
| microcrystalline cellulose | 5.0% |
| china clay | 2.0% |
| PEG 4000 (molten) | 13.0 |
| citric acid (anhydrous) | 15.0% |
| sodium bicarbonate | to 100% |

EXAMPLE 7

| 0.5% Pyrethrins Granules | |
|---|---|
| 2.5 pyrethrins dust concentrate | 2.0% |
| sodium dioctylsulphosuccinate | 15.0% |
| microcrystalline cellulose | 5.0% |
| china clay | 2.0% |
| PEG 4000 (molten) | 13.0 |
| citric acid (anhydrous) | 15.0% |
| sodium bicarbonate | to 100% |

EXAMPLE 8

| 35% Propanil Tablets | |
|---|---|
| 35% propanil technical | 35.0% |
| sodium dioctylsulphosuccinate | 15.0% |
| polyvinylpyrrolidone | 4.0% |
| silica | 5.0% |
| magnesium stearate | 1.0% |
| microcrystalline cellulose | 9.0% |
| citric acid (anhydrous) | 7.5% |
| sodium bicarbonate | to 100% |

EXAMPLE 9

| 35% Propanil Granules | |
|---|---|
| 35% Propanil technical | 35.0% |
| sodium dioctylsulphosuccinate | 15.0% |
| microcrystalline cellulose | 5.0% |
| china clay | 2.0% |
| PEG 4000 | 13.0% |
| citric acid (anhydrous) | 7.5% |
| sodium bicarbonate | to 100% |

EXAMPLE 10

Controlled-Release Tubes & Cartridges

Controlled-release tubes are solid biodegradable cardboard tubes packed with 3-4 small quantities of granules each separated by a thin layer of water soluble wax. The granules used are the 15% effervescent granules as described in the Example 3. The method of application is simply to toss one of the tubes into a mosquito infested pond. After a short time the water soluble wax plug in the top of the tube dissolves allowing the first batch of granules to come in contact with the water. The granules rise to the water surface, effervesce and disperse the Bt (or other insecticide) across the surface. Gradually over the next week to 10 days the second layer of water soluble wax dissolves allowing release of the second dose of insecticide and so on. The typical persistence of Bt in the environment is 2-3 days.

The water soluble wax normally used in polyethylene glycol (PEG) molecular weight 4000. Other molecular weight PEGs have been used and as a general rule the higher molecular weight waxes dissolve more slowly giving a longer interval between doses. Other factors affecting rate or time of release are water temperature (higher temperature leads to quicker release) and was thickness (thinner wax leads to quicker release). With these parameters in mind, a suitable formulation can be provided for any particular application.

We claim:

1. A pesticidal formulation in tablet, granule, or pellet form for water treatment comprising:

a. an effective amount of at least one biological pesticidal ingredient;
b. at least one effervescent-initiating component;
c. at least one surface active dispersant;
d. a lubricant;
e. a binder;
f. a disintegrant; and
g. a low density buoyancy aid wherein said biological pesticidal ingredient is a Bacillus thuringiensis var. israelensis preparation and wherein said pesticidal formulation is formulated so as to disperse said pesticidal ingredient at or near the surface of the water to be treated.

2. The formulation according to claim 1 wherein said surface active dispersant is an anionic surfactant selected from the group consisting of an alkylbenzene sulphonate, an alcohol sulfate, an ether sulfate, a phosphate ester, a sulphosuccinate, an alane sulphonate, an olefin sulphonate, a petroleum sulphonate, a sarcosinate and a taurate.

3. A controlled-release formulation for water treatment comprising:

1. a pesticidal formulation comprising:
   a. an effective amount of at least one biological pesticidal ingredient;
   b. at least one effervescent-initiating component;
   c. at least one surface active dispersant;
   d. a lubricant;
   e. a binder;
   f. a disintegrant;
   g. a low density buoyancy aid, and
2. at least one water-soluble polymer wherein said biological pesticidal ingredient is a Bacillus thuringiensis var. israelensis preparation.

4. a pesticidal formulation according to claims 1 or 3 wherein said disintegrant comprises polyvinylpyrrolidone.

5. A pesticidal formulation according to claims 1 or 3 wherein said low density buoyancy aid comprises colloidal silica.

6. The formulation according to claim 3 wherein said surface active dispersant is an anionic surfactant selected from the group consisting of an alkylbenzene sulphonate, an alcohol sulfate, an ether sulfate, a phosphate ester, a sulphosuccinate, an alkane sulphonate, an olefin sulphonate, a petroleum sulphonate, a sarcosinate and a taurate.

7. A pesticidal formulation according to claim 2 or claim 6 wherein said surface active dispersant comprises sodium dioctylsulphosuccinate.

8. The formulation accordign to claim 3 wherein said water-soluble polymer comprises a polyethylene glycol polymer.

9. A method of controlling water-borne pests comprising dosing water with a pesticidal formulation comprising:

a: an effective amount of at least one biological pesticidal ingredient;
b. at least one effervescent-initiating component;
c. at least one surface active dispersant;
d. a lubricant;
e. a binder;
f. a disintegrant; and
g. a low density buoyancy aid wherein said biological pesticidal ingredient is a Bacillus thuringiensis var. israelensis preparation and wherein said persticidal formulation is formulated so as to disperse said pesticidal ingredient at or near the surface of the water to be treated.

10. A method of controlling water-borne pests comprising dosing water with a controlled-release formulation according to claim 3.

11. A method of controlling water-borne pests by dosing infested water with a pesticidal formulation according to claim 1.

* * * * *